United States Patent [19]

Ebizawa et al.

[11] Patent Number: 4,507,192
[45] Date of Patent: Mar. 26, 1985

[54] OXYGEN SENSOR FOR EXHAUST GAS OF INTERNAL COMBUSTION ENGINE

[75] Inventors: Akio Ebizawa, Iwakura; Hisaharu Nishio, Tokai, both of Japan

[73] Assignee: NGK Spark Plug Co., Ltd., Nagoya, Japan

[21] Appl. No.: 569,936

[22] Filed: Jan. 12, 1984

Related U.S. Application Data

[63] Continuation of Ser. No. 342,815, Jan. 26, 1982, abandoned.

[30] Foreign Application Priority Data

Jun. 1, 1981 [JP] Japan .................................. 56-84668

[51] Int. Cl.³ ........................................... G01N 27/30
[52] U.S. Cl. .................................................. 204/428
[58] Field of Search ................ 204/1 S, 409, 410, 421, 204/424, 428

[56] References Cited

U.S. PATENT DOCUMENTS 4,065,372 12/1977 Hacker et al. .................... 204/195 S
4,184,934 1/1980 Bode et al. ...................... 204/195 S

FOREIGN PATENT DOCUMENTS 2326086 12/1974 Fed. Rep. of Germany .
2348505 4/1975 Fed. Rep. of Germany .
1469698 4/1975 United Kingdom .

Primary Examiner—John F. Niebling
Assistant Examiner—B. J. Boggs, Jr.
Attorney, Agent, or Firm—Fleit, Jacobson, Cohn & Price

[57] ABSTRACT

The oxygen sensor for exhaust gas of internal combustion engine includes a solid electrolyte tube having an inner electrode coated on the inner surface of said electrolyte tube outer electrode formed on outer surface of said electrolyte tube and disposed on the outside surface thereof so as to come in contact with exhaust gas and a metallic protective tube coaxially surrounding said electrode with a spacing therefrom. The sidewall of the protective tube has two similarly arranged matrices of holes, each hole being made by cutting an arcuate edge on the sidewall and bending the thus cut portion toward the inside of the protective tube, and the holes of one matrix are interposed among the holes of the other matrix while being offset therefrom in both the longitudinal and circumferential directions of the protective tube.

3 Claims, 4 Drawing Figures

OXYGEN SENSOR FOR EXHAUST GAS OF INTERNAL COMBUSTION ENGINE

This application is a continuation of application Ser. No. 342,815, filed Jan. 26, 1982 now abandoned.

BACKGROUND OF THE INVENTION

1. Field of the Invention

This invention relates to a cell type oxygen sensor for measuring oxygen concentration in exhaust gas from an internal combustion engine such as the oxygen concentration after chemical equilibrium is reached in the exhaust gas.

2. Description of the Prior Art

A typical oxygen sensor for exhaust gas in the prior art which is used at the present comprises a solid electrolyte tube with a bottom at an end, an inner electrode coated on the inner surface of said electrolyte tube so as to contact with fresh air as reference gas, an outer electrode coated on the outer surface of said electrolyte tube so as to contact with exhaust gas, a metallic housing tube holding said solid electrolyte tube while allowing exposure of said outer surface at the bottom thereof to the exhaust gas, a protective means having a pipe coaxially extending from one end of the housing tube so as to surround the bottom side of said solid electrolyte tube, and a gas passage defined in said pipe for restricting direct collision of the exhaust gas with the outer surface of said solid electrolyte tube. The protective means prevents impulsive hot exhaust gas stream and fine particle in the exhaust gas from directly striking and colliding with the porous membrane type electrode layer coated on the outer surface of said solid electrolyte tube, so as to avoid comparatively quick deterioration of the performance of the electrode.

One typical form of the conventional protective means includes a pair of metallic pipes with different diameters, each of said pipes having a plurality of holes bored through the sidewall thereof, which metallic pipes are coaxially connected while offsetting the holes of one pipe from the holes of the other pipe as shown in U.S. Pat. No. 4,065,372. The protective means of such two-pipe type has shortcomings in that the thermal mass of the protective means tends to become large, despite that a large thermal mass is against the demand for a low activating temperature (i.e. operation-starting temperature) of the exhaust gas sensor, and that the protective means is rather costly. Another form of the conventional protective means consists of one metallic pipe whose sidewall is severed along the long line extending in the axial direction thereof, and a plurality of long but narrow holes are formed with spacings in the circumferential direction of the pipe by bending the sidewall inwardly along one side of each of said long lines so as to make openings substantially in the tangential directions. The protective means of the one-pipe type has shortcomings in that the narrowness of the holes tends to increase resistance against gas flow therethrough despite the comparatively large length thereof resulting in a poor efficiency of exchanging gas, and that such narrow holes are difficult to make wider because if one tries to bend the sidewall deeper toward the inside of the pipe for broadening the openings, the axially long sidewall portions between the adjacent holes are apt to be deformed to make the bending work difficult.

SUMMARY OF THE INVENTION

Therefore, an object of the present invention is to obviate the aforesaid shortcomings of the prior art by providing a novel exhaust gas sensor. To fulfil the object, the oxygen sensor of exhaust gas in the present invention uses a protective tube adapted to introduce exhaust gas into the inside thereof while deflecting flows of the exhaust gas in the circumferential direction thereof, which protective tube has a small resistance to the incoming and outgoing exhaust gas flows and a small mass, so that the activating temperature of the oxygen sensor of exhaust gas is low. The protective tube used in the present invention can be machined easily with a high finish accuracy while maintaining a high strength.

More specifically, the invention provides an oxygen sensor for an exhaust gas of an internal combustion engine, which sensor comprises a solid electrolyte tube having a bottom at one end thereof, an inner electrode coated on the inner surface of said electrolyte tube so as to contact with fresh air as reference gas, an outer electrode coated on the outer surface of said electrolyte tube so as to contact with the exhaust gas, a metallic housing tube holding said solid electrolyte tube while allowing exposure of said outer bottom surface thereof to the exhaust gas, a metallic protective tube coaxially extending from one end of the metallic housing tube so as to surround the outer bottom surface of the solid electrolyte tube, and a plurality of holes bored through sidewall of said protective tube by cutting selected portions of said sidewall and inwardly bending those sidewall portions which are adjacent to the thus cut portions of said sidewall so as to form exhaust-gas-flow deflecting means, characterized in that said holes are arranged in two matrices, each of the two matrices having at least two rows of the holes with inter-row spacings in the longitudinal direction of the protective tube and at least four columns of the holes with inter-column spacings in the circumferential direction of the protective tube, the holes of one of said two matrices being interposed among the holes of the other one of said two matrices while being longitudinally and circumferentially offset therefrom, each of said holes having an exhaust-gas-flow deflecting lug extending inwardly from the sidewall of the protective tube while defining a chord at the foot of the lug, each of the holes having an arcuate edge facing said chord, the arcuate edges of all the holes extending in one common circumferential direction from the corresponding chords thereof. The arcuate edge of each hole of the sidewall of protective tube may be substantially semicircular or substantially semi-elliptic.

In a preferred embodiment of the invention, the holes of one of the two matrices are offset from the holes of the other one of the two matrices in the longitudinal direction of the electrolyte tube by one half of said inter-row spacing of each matrix and in the circumferential direction of the electrolyte tube by one half of said inter-column spacing of each matrix.

BRIEF DESCRIPTION OF THE DRAWINGS

For a better understanding of the invention, reference is made to the accompanying drawings, in which.

Throughout different views of the drawings, 1 is a solid electrolyte tube, 1a is a flange portion, 1b is a bottom, 1c is a reference-gas-side inner electrode, 1d is an objective-gas-side outer electrode, 1e is an electrode protecting layer, 2 is a metallic housing tube, 2a is a shelf portion, 2b is a screw thread, 3 is an exhaust gas pipe, 4 is an upper cap, 4a is a vent hole, 5 is a metallic protective tube, 5a is a bottom, 5b is a flange, 5c is sidewall, 6 is a hole, 6a is a semicircular opening, 6b is a lug, 10 is a die, 10a is a groove, and 11 is a punch.

DESCRIPTION OF THE PREFERRED EMBODIMENT

Figure 1:
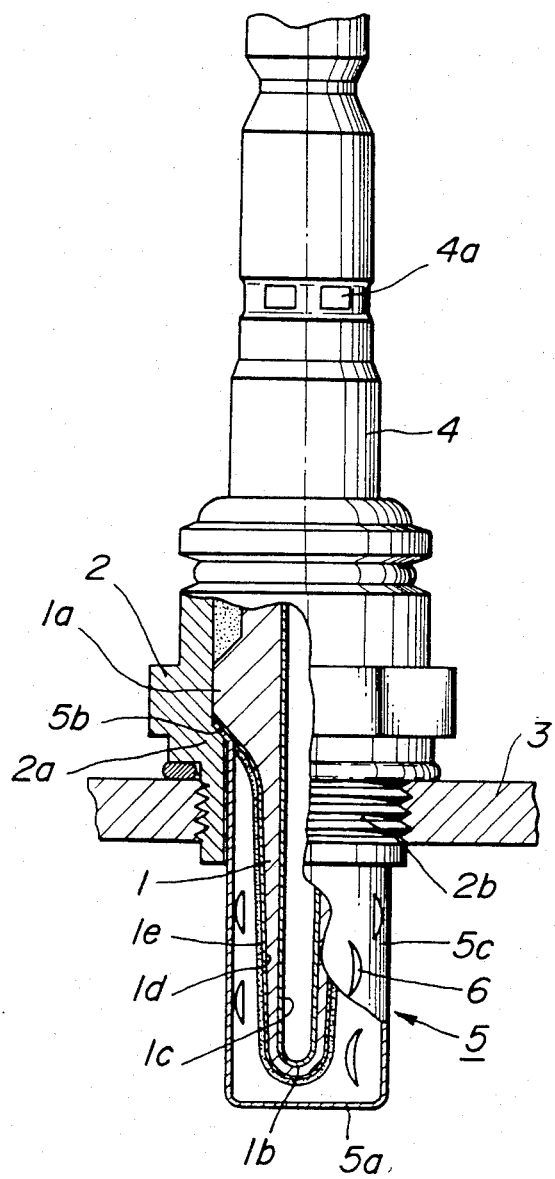
FIG. 1 is a side view, with a part in section, of an embodiment of the exhaust gas sensor according to the present invention.

Referring to FIG. 1, a solid electrolyte tube 1 having a flange portion 1a and a bottom 1b is made of a solid electrolyte of oxygen-ion conductive type, preferably a sintered body of the so-called partially stabilized zirconium oxide with a stabilizing oxide such as yttria. A reference-gas-side inner electrode 1c of this embodiment is a porous platinum layer deposited on the inner surface of the solid electrolyte tube 1, and an object-gas-side outer electrode 1d is made of a porous platinum layer deposited on the outer surface of the solid electrolyte tube 1 from the flange portion 1a to the bottom 1b thereof. Preferably, the object-gas-side outer electrode 1d is provided by chemical plating treatment of platinum followed by electric plating and treatment of platinum followed by electric plating and formation of a large number of sizeable holes through heat treatment, so as to cause firm adhesion of the electrode to the outer surface of the solid electrolyte tube 1. Furthermore, it is preferable to form sturdy undulations on that outer surface of the solid electrolyte tube 1 where the object-gas-side outer electrode 1d is to be provided. An electrode protecting layer 1e is formed, for instance, by hot spraying of ceramics powder such as spinel powder on the object-gas-side outer electrode 1d through flame spraying process or the like, so as to firmly deposit a porous ceramic layer on the outer surface of the solid electrolyte tube 1. A metallic housing tube 2 has a generally tubular shape and includes an annular shelf portion 2a extending inwardly from the inner surface thereof toward the central axis thereof. The shelf portion 2a holds the flange portion 1a of the solid electrolyte tube 1 by conventional means, for instance, by direct or indirect abutting of the flange portion 1a to the shelf portion 2a. The metallic housing tube 2 is adapted to be electrically connected to the object-gas-side outer electrode 1d at the shelf portion 2a, so that the metallic housing tube 2 acts as a terminal of the exhaust gas sensor. Screw thread 2b is formed at the lower outside surface of the metallic housing tube 2, so that the metallic housing tube 2 is screwed into and tightly secured to a tapped hole of an exhaust pipe 3 while allowing exposure of the outer bottom surface of the solid electrolyte tube 1 to the exhaust gas in the pipe 3.

The reference-gas-side inner electrode 1c at the inside of the solid electrolyte tube 1 is electrically insulated from the metallic housing tube 2 and connected to an outside circuit (not shown) through a lead wire (not shown) and a terminal (not shown). An upper cap 4 with vent holes 4a is integrally secured to the metallic housing tube 2 so as to extend upwardly therefrom, and the reference-gas-side inner electrode 1c is kept in contact with the fresh air in the inside of the solid electrolyte tube 1 communicating with the atmosphere through the vent hole 4a of the upper cap 4.

To prevent the exhaust gas from direct collision with the outer surface of the solid electrolyte tube 1, a metallic protective tube 5 coaxially extends from the lower end of said shelf portion 2a of the metallic housing tube 2 so as to surround the electrolyte tube 1. In the embodiment of FIG. 1, the protective tube 5 is a thin-wall stainless steel tube made by deep drawing so as to provide a bottom 5a at a closed end thereof and a flange 5b at an open end thereof. The flange 5b of the protective tube 5 is held between the shelf portion 2a of the housing tube 2 and the flange portion 1a of the solid electrolyte tube 1, whereby the protective tube 5 is secured to the housing tube 2. It is also possible to directly connect the protective tube 5 to one end of the housing tube 2 for instance by welding.

Figure 2A:
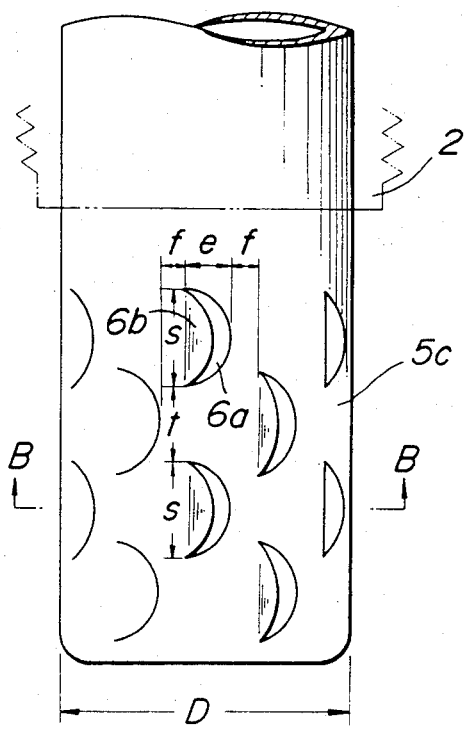
FIG. 2A is an enlarged side view of an essential portion of a protective tube in the gas sensor of FIG. 1.
Figure 2B:
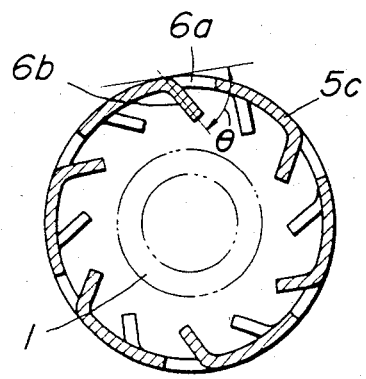
FIG. 2B is a schematic sectional view taken along the line B—B of FIG. 2A.

A large number of holes 6 are bored through sidewall 5c of the protective tube 5. All the holes 6 have arcuate portions which are convex toward a common circumferential direction of the protective tube 5. Referring to FIG. 1 and FIGS. 2A and 2B, the arcuate portion of each hole 6 of the illustrated embodiment forms a semicircular opening 6a, which opening 6a is made by cutting a semicircular arc on the sidewall 5c and bending an arcuate portion adjacent the thus cut arc toward the inside of the protective tube 5 by a comparatively large angle so as to form a lug 6b. The shape of the arc at the edge of the hole 6a is not required to be semicircular, and it can be semi-elliptic or other smoothly curved arcuate shape.

Referring to FIGS. 2A and 2B, the large number of holes 6 are disposed in two interposed matrices; namely, each of the two matrices has at least two rows of holes 6 (two rows in the embodiment) with an inter-row spacing t in the longitudinal direction of the protective tube 5 between the adjacent rows and at least four columns of the holes 6 (six columns in the embodiment) with an inter-column spacing (e+2f) in the circumferential direction of the protective tube 5 between the adjacent columns, and the holes 6 of one of the two matrices are interposed among the holes 6 of the other one of the two matrices while being longitudinally and circumferentially offset therefrom, preferably by one halves of the aforesaid inter-row and inter-column spacings respectively. As a result, the holes 6 are disposed in a zigzag fashion on the sidewall 5c of the protective tube 5. A practical example of the protective tube 5 of the oxygen sensor for exhaust gas of the invention has a protective tube outside diameter D of 12 mm, a sidewall thickness of 0.5 mm, a chord length s of the hole 6 of 4 mm, a distance e of 2 mm from the chord to the apex of the arc, a longitudinal inter-row spacing t of 3 mm between adjacent rows of the holes 6, a circumferential spacing f of about 1 mm between nearest two holes, and an angle $\theta$ of about 60° between the lug 6b and a tangential plane to the protective tube 5 at the chord defined by the foot of the lug.

Preferably, the protective tube 5 is made of stainless steel, and the ratio of the thickness of the sidewall 5c and the outside diameter D of the protective tube 5 is preferably 0.02 to 0.05, for instance, a thickness of about 0.3 to 0.5 mm for the outside diameter D of 10 to 13 mm.

Figure 3:
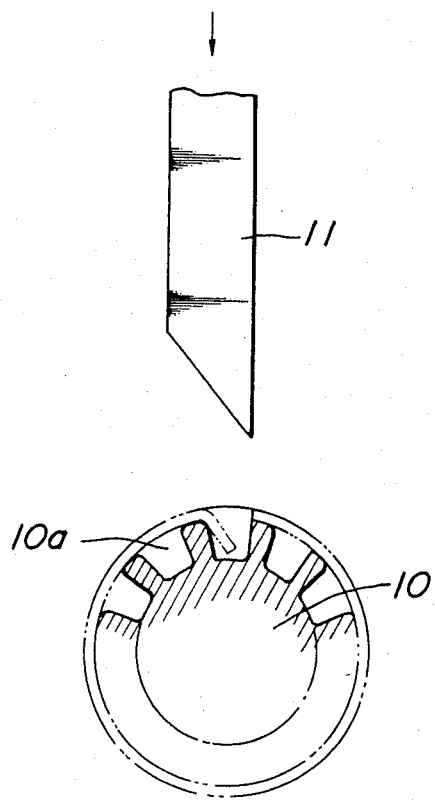
FIG. 3 is a diagrammatic illustration of a process of producing the protective tube of the exhaust gas sensor.

Now, a preferred process for making the protective tube 5 of the oxygen sensor for exhaust gas of the present invention will be described by referring to FIG. 3. A cylindrical die 10 having an outside diameter which is slightly smaller than the inside diameter of a protective tube 5 to be produced is slidably fitted in a tube material therefor whose sidewall has no holes. The die 10 has a predetermined number of linear grooves 10a cut on the circumference thereof so as to extend in the longitudinal direction thereof. After the die 10 is inserted into the tube material with the aforesaid inside diameter, a punch assembly having a certain number of punches 11 aligned in the longitudinal direction of the die 10 with preset spacings therebetween is pressed into the groove 10a of the die 10, so that one column of the holes 6 of one matrix can be bored by one pressing stroke of the punch assembly. Then, the tube material with the die 10 fitted therein is turned until the next groove 10a comes under the assembly of the punches 11 and the next column of the holes 6 can be bored by one pressing of the punch assembly. Thus, one matrix of the holes 6 can be completed by repeating similar pressing until the tube material with the die 10 is turned by one revolution. Thereafter, the tube material with the die 10 inserted therein is shifted longitudinally and circumferentially by the amounts corresponding to the offsets between the two matrices, so that the other matrix of the holes can be bored by repeating the same pressing as that of the first matrix from the thus shifted position. Whereby, all the holes 6 of the protective tube 5 can be bored very easily without causing any deformation extraneous to the function of the oxygen sensor for exhaust gas. After completion of the pressing for boring the holes 6, the die 10 can be easily removed from the protective tube 5 with the holes 6 thus bored.

The inventors have prepared a number of oxygen sensors for exhaust gas having the protective tubes 5 with the holes 6 of various dimensions and dispositions, and carried out a series of tests on the thus prepared oxygen sensors for exhaust gas by connecting them to actual internal combustion engines. The tests included evaluation tests of initial activation performance and high-temperature endurance tests to prove that the metallic protective tube 5 was free from deformations and cracks at elevated temperatures, and the above-mentioned evaluation tests were carried out by measuring the time from a moment of suddenly mounting the oxygen sensor onto the sensor-mount hole of an exhaust gas pipe carrying an exhaust gas stream of fuel-rich atmosphere type at 350° C. to a moment when the sensor output increased in excess of 700 mV. As a result, it was found that the preferable angle $\theta$ between the bent lug 6b of the hole 6 and a tangential plane to the circumference of the protective tube 5 at the chord at the foot of lug 6b is between 40° to 70°, and the lug 6b should be bent toward the inside of the protective tube 5. The inventors also found that the following conditions are particularly suitable for achieving an initial activation time of less than 3 minutes and large opening areas of the holes 6 without deforming the tube 5; namely, $e = (\frac{3}{8} \text{ to } 1)s$,
$t = (\frac{1}{2} \text{ to } 4/3)s$, and
$f = (\frac{1}{4} \text{ to } \frac{1}{2})s$, here, s is the length of the chord of the hole 6, e is the distance from the chord to the apex of the arcuate edge of the hole 6, t is the longitudinal inter-row spacing between adjacent rows of the holes 6 in one matrix, and f is the circumferential spacing between the nearest two holes 6. Accordingly, in the case of a typical thin-wall protective tube 5 with an outside diameter D of about 10 to 13 mm, the chord lengths s can be 3 to 4 mm, and the circumferential spacing f between the nearest two holes 6 can be as small as 0.5 to 2 mm. Consequently, the invention provides a metallic protective tube 5 having a better initial activation performance, i.e., a lower activation temperature, as compared with that of a conventional protective tube whose side-wall is severed along the long lines extending in the axial direction thereof so as to form a plurality of long slit-like holes with spacings in the circumferential direction thereof.

In the illustrated embodiment, the bottom 5a of the protective tube 5 does not have any hole, but it is also possible in the present invention to bore suitable holes on the bottom 5a or to eliminate the bottom 5a completely.

As described in the foregoing, the oxygen sensor for exhaust gas according to the present invention uses a protective tube whose sidewall has a plurality of holes disposed in a zigzag fashion, each hole being made by cutting an arcuate line, preferably a semicircular or semi-elliptic arc, on the sidewall, and bending the thus cut portion of the sidewall toward the inside of the protective tube to such an extent that the thus bent lug makes an angle of 40° to 70° relative to a tangential plane to the circumference of the protective tube at the foot of the lug, the arcuate lines of all the holes being convex toward one common circumferential direction of the protective tube, said lug acting as an exhaust gas deflecting lug, so that as compared with the prior art, a large amount of the exhaust gas flows into and out of the protective tube at a high efficiency. Besides, the oxygen sensor for exhaust gas of the invention has such a small thermal mass that the activating temperature of the oxygen sensor for exhaust gas can be kept low. Thus, the invention provides outstanding effects in that the protective tube being used in the invention is easy to manufacture without causing any deformation of the tube during manufacture thereof, and yet the protective tube has a high mechanical strength.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. An oxygen sensor for exhaust gas of an internal combustion engine comprising:
    a solid electrolyte tube having a bottom at one bottom end thereof, a reference-gas-side inner electrode coated on the inner surface of said solid electrolyte tube so as to be kept in contact with fresh air, an object-gas-side outer electrode coated on the outer surface of said electrolyte tube so as to come in contact with the exhaust gas, a metallic housing tube holding said solid electrolyte tube and allowing exposure of said outer bottom surface thereof to the exhaust gas, a metallic protective tube coaxially extending from one end of an annular shelf of said housing tube so as to surround the bottom of said solid electrolyte tube, a plurality of holes bored through the sidewall of said protective tube so as to have convex arcuate edges relative to one common circumferential direction of the protective tube, and a plurality of lugs being bent at said holes toward the inside of said protective tube so as to form chords at feet of the thus bent lugs, the chords facing said arcuate edges, each of said holes and said lugs being similarly oriented relative to the protective tube, each of said lugs being equally bent toward the inside of the protective tube by the same angle of 40° to 70° relative to a tangential plane to the circumference of said protective tube at said chord defined by the foot of said lug so as to deflect flow of the exhaust gas inwardly in a transverse circumferential direction relative to the longitudinal direction of the electrolyte tube, said holes being arranged in two matrices, each of said two matrices having at least two rows of the holes with inter-row spacings in the longitudinal direction of the protective tube and at least four columns of the holes with inter-column spacings in the circumferential direction of the protective tube, the holes of one of said two matrices being interposed among the holes of the other one of said two matrices and being longitudinally and circumferentially offset therefrom, the holes of one of the two matrices being offset from the holes of the other one of the two matrices in the longitudinal direction of the solid electrolyte tube by one half of said longitudinal inter-row spacing of each matrix and in the circumferential direction of the solid electrolyte tube by one half of said circumferential inter-column spacing of each matrix, and said holes satisfying the following conditions:

$s = (1/5 \text{ to } 2/5)D$,
$e = (\frac{3}{8} \text{ to } 1)s$,
$t = (\frac{1}{2} \text{ to } 4/3)s$, and
$f = (\frac{1}{4} \text{ to } \frac{1}{2})s$, wherein "s" is the length of said chord, "D" is the outside diameter of said protective tube, "e" is a distance from said chord to the apex of said arcuate edge, "t" is the longitudinal inter-row spacing between adjacent rows of the holes in each of said matrices, and "f" is the circumferential spacing between the nearest two holes.

2. An oxygen sensor for exhaust gas as defined in claim 1, wherein said arcuate edge of each of said holes is semicircular.

3. An oxygen sensor for exhaust gas as defined in claim 1, wherein said arcuate edge of each of said holes is semi-elliptic.

* * * * *